(12) United States Patent
Mango

(10) Patent No.: US 7,153,688 B2
(45) Date of Patent: Dec. 26, 2006

(54) ROCK ASSAY FOR PREDICTING OIL OR GAS IN TARGET RESERVOIRS

(75) Inventor: Frank D. Mango, Houston, TX (US)

(73) Assignee: Petroleum Habitats, L.L.C, Houston, TX (US)

( * ) Notice: Subject to any disclaimer, the term of this patent is extended or adjusted under 35 U.S.C. 154(b) by 90 days.

(21) Appl. No.: 11/006,159

(22) Filed: Dec. 7, 2004

(65) Prior Publication Data
US 2006/0121615 A1 Jun. 8, 2006

(51) Int. Cl.
G01N 33/24 (2006.01)
G01N 33/22 (2006.01)

(52) U.S. Cl. .............. 436/32; 73/152.09; 73/152.11; 436/25; 436/29; 436/31; 436/141

(58) Field of Classification Search ............ 436/25–26, 436/29, 31–32, 141; 73/152.09, 152.11
See application file for complete search history.

(56) References Cited

U.S. PATENT DOCUMENTS

| | | | | |
|---|---|---|---|---|
| 2,768,793 A | * | 10/1956 | Bonner | 241/68 |
| 2,854,396 A | * | 9/1958 | Hunt et al. | 208/426 |
| 3,719,453 A | * | 3/1973 | Erdman | 436/27 |
| 3,934,455 A | * | 1/1976 | Harrisberger | 436/5 |
| 4,352,673 A | * | 10/1982 | Espitalie et al. | 436/145 |
| 4,681,854 A | * | 7/1987 | Feazel | 436/31 |
| 4,792,526 A | * | 12/1988 | Ouellette et al. | 436/29 |
| 4,798,805 A | * | 1/1989 | Issenmann | 436/157 |
| 5,082,787 A | * | 1/1992 | Nolte et al. | 436/31 |
| 5,389,550 A | * | 2/1995 | Ishida et al. | 436/32 |

OTHER PUBLICATIONS

Kravtsov, A. I., Zakonomern. Obraz, Razmeshcheniya Prom. Mestorozhd. Nefti Gaza (1975), 38-48. Editor(s): Dolenko, G. N. Publisher: "Naukova Dumka", Kiev, USSR.*
Espitalie, J. et al, Organic Geochemistry 1984, 6, 365-379 and 381-382.*
Nikol'skii, N. S., Vulkanologiya i Seismologiya 1984, 45-58.*
Ungerer, P. et al, Nature 1987, 327, 52-54.*
Dembicki, H., Jr., Organic Geochemistry 1992, 18, 531-539.*
Braun, R. L. et al, Energy & Fuels 1992, 6, 468-474.*
Barth, T. et al, Energy & Fuels 1993, 7, 100-110.*
Mango, F., 1993, OSTI as DE93019698; NTIS.*
Mango, F. D. et al, Nature 1994, 368, 536-538.*
Reynolds, J. G. et al, Organic Geochemistry 1995, 23, 11-19.*
McNeil, R. I. et al, Energy & Fuels 1996, 10, 60-67.*
Mango, F. D., Organic Geochemistry 1996, 24, 977-984.*
Mango, F., 1993, OSTI as DE-FG05-92ER14295; NTIS.*
Knauss, K. G. et al, Organic Geochemistry 1997, 27, 477-496.*

(Continued)

Primary Examiner—Arlen Soderquist
(74) Attorney, Agent, or Firm—Robert C. Shaddox; Winstead Sechrest & Minick P.C.

(57) ABSTRACT

The present invention relates to assays for ascribing catalytic activity to rock samples by virtue of zero-valent transition metals potentially being present within the sample. Embodiments of the present invention are generally directed to novel assays for measuring intrinsic paleocatalytic activities (k) of sedimentary rocks for converting oil to gas and projecting the activities to the subsurface based on the measured linear relationship between ln(k) and temperature (T).

97 Claims, 8 Drawing Sheets

OTHER PUBLICATIONS

Mango, F. D. et al, Geochimica et Cosmochimica Acta 1997, 61, 5347-5350.*
Dieckmann, V. et al, Fuel 1997, 77, 23-31.*
Schaefer, R. G. et al, Chemical Geology 1999, 156, 41-65.*
Michels, R. et al, Marine and Petroleum Geology 2002, 19, 589-599.*
Ramaswamy, G., Oil & Gas Journal 2002, 100, 32-36.*
Starobinets, I. S. et al, Trudy—Institut Geologii i Razvedki Neftyanykh i Gazovykh Mestorozhdenii 1975, 17, 108-114.*
Rafiqul, I., Journal of Bangladesh Academy of Sciences 1995, 19, 97-104.*
Jin, Q. et al, Applied Geochemistry 1999, 14, 547-558.*
Jin, Q. et al, Dizhi Kexue 2003, 38, 342-349.*

* cited by examiner

ROCK ASSAY FOR PREDICTING OIL OR GAS IN TARGET RESERVOIRS

CROSS REFERENCE TO RELATED APPLICATIONS

This present Application is related to commonly assigned co-pending U.S. patent application Ser. No. 10/830,266, filed Apr. 21, 2004.

TECHNICAL FIELD

The present invention relates generally to assays for rock samples potentially comprising zero-valent transition metals, and specifically to assays for ascribing catalytic activity to rock samples by virtue of zero-valent transition metals potentially being present within the sample. An understanding of such catalytic activity is useful in predicting the distribution of oil and gas in sedimentary basins and thus has revolutionary potential in oil and gas exploration.

BACKGROUND INFORMATION

Oil progresses to natural gas in deep sedimentary basins. This process, hereafter referred to as "oil-to-gas," is believed to be the major source of natural gas in the earth (Hunt, *Petroleum Geochemistry and Geology*, $2^{nd}$ ed., W. H. Freeman, New York., Chapter 7, 1996). Knowing when and how this process occurs is the key to predicting the distribution of oil and gas with depth. The conventional view is that oil thermally cracks to gas (thermal gas) at temperatures between 150° C. and 200° C., the observed temperature range where most oil-to-gas occurs. Various kinetic models (thermal models) based on this theory have had only marginal success, however, and there are glaring contradictions. Oil, for example, is found in deep reservoirs (>20,000 ft) at temperatures where it should not exist (Paine et al., "Geology of natural gas in South Louisiana," American Association of Petroleum Geologists, Memoir 9, Volume 1, Natural Gases of North America, Beebe, B. W., Editor, 376–581, 1968; Price, "Thermal stability of hydrocarbons in nature: Limits, evidence, characteristics, and possible controls," *Geochimica et Cosmochimica Acta*, 57:3261–3280, 1993), and giant deposits of so-called thermal gas exist in shallow reservoirs that cannot be explained by the thermal model without invoking long-range migration from deeper horizons (Littke et al., "Gas generation and accumulation in the West Siberian basin," *AAPG Bull.*, 83:1642–1665, 1999).

There is now mounting scientific evidence against the thermal models. From a series of laboratory experiments under realistic conditions (Domine et al., "Towards a new method of geochemical kinetic modeling: implications for the stability of crude oils," *Organic Geochemistry*, 28:597–612, 1998; Domine et al., "Up to what temperature is petroleum stable? New insights from 5200 free radical reaction model," *Organic Geochemistry*, 33:1487–1499, 2002), evidence now suggests that oil should not crack to gas over geologic time at temperatures between 150° C. and 200° C., the range within which most so-called thermal gas is formed, a conclusion supported by numerous other studies (Mallinson et al., "Detailed chemical kinetics study of the role of pressure in butane pyrolysis," *Industrial & Engineering Chemistry, Research*, 31:37–45, 1992; Burnham et al., "Unraveling the kinetics of petroleum destruction by using $1,2^{13}C$ isotopically labeled dopants," *Energy & Fuels*, 9:190–191, 1995; Jackson et al., "Temperature and pressure dependence of n-hexadecane cracking," *Organic Geochemistry*, 23:941–953, 1995). Moreover, the gas produced in oil cracking is severely depleted in methane and does not resemble natural gas as it is distributed in the earth (Mango, "The origin of light hydrocarbons," *Geochimica et Cosmochimica Acta*, 64:1265–1277, 2001).

Catalysis by transition metals is an alternative explanation for oil-to-gas (Mango, "Transition metal catalysis in the generation of petroleum and natural gas," *Geochimica et Cosmochimica Acta*. 56:553–555, 1992), and there is experimental evidence supporting it. Crude oils are converted to gas over zero-valent transition metals (ZVTM) (e.g., Ni, Co, and Fe) under moderate laboratory conditions (150–200° C.) and the products are identical to natural gas in molecular and isotopic composition (Mango and Hightower, "The catalytic decomposition of petroleum into natural gas," *Geochimica et Cosmochimica Acta*, 61:5347–5350, 1997; Mango and Elrod, "The carbon isotopic composition of catalytic gas: A comparative analysis with natural gas," *Geochimica et Cosmochimica Acta*, 63:1097–1106, 1998; Mango, "The origin of light hydrocarbons," *Geochimica et Cosmochimica Acta*, 64:1265–1277, 2000).

The above-described experiments are highly relevant to the generation of natural gas in sedimentary basins. Transition metals are common in sedimentary rocks (Boggs, S., Jr., *Principles of Sedimentology and Stratigraphy*, $2^{nd}$ ed., Prentice-Hall, Inc., NJ, pages 165 & 195, 1995), and could become catalytically active (i.e., reduced to zero-valencies) given the reducing conditions of petroleum habitats (Mango, "The light hydrocarbons in petroleum: a critical review," *Organic Geochemistry*, 26:417–440, 1997; Mango, "The origin of light hydrocarbons," *Geochimica et Cosmochimica Acta*, 64:1265–1277, 2000; Medina et al., "Low temperature iron- and nickel-catalyzed reactions leading to coalbed gas formation," *Geochimica et Cosmochimica Acta*, 64:643–649, 2000; Seewald, "Organic-inorganic interactions in petroleum-producing sedimentary basins," *Nature*, 426:327–333, 2003). All requisites are in place: transition metal oxides in sufficient amounts to promote the reaction and enough hydrogen to activate them to zero-valencies and drive the reaction at subsurface temperatures (Mango, "The origin of light hydrocarbons," *Geochimica et Cosmochimica Acta*, 64:1265–1277, 2000).

Catalysis may be the source of the huge gas deposits in the Gulf Coast geosyncline of south Louisiana (Paine et al., "Geology of natural gas in South Louisiana," American Association of Petroleum Geologists, Memoir 9, Volume 1, Natural Gases of North America, Beebe, B. W., Editor, 376–581, 1968). Oil is generally found at depths above 10,000 feet and gas is generally found below such depths, consistent with the thermal model. However, gas probabilities are also a strong function of reservoir composition: low in pure sandstone and high in sandstones interbedded with outer-neritic shales that are often enriched in transition metals (Mann and Stein, "Organic facies variations, source rock potential, and sea level changes in Cretaceous black shales of the Quebrada Ocal, Upper Magdalena Valley, Colombia," *American Association of Petroleum Geologists Bulletin*, 81:556–576, 1997; Cruickshank and Rowland, "Mineral deposits at the shelfbreak," SEPM Special Publication No. 33, 429–436, 1983).

Given high enough temperatures and hydrogen partial pressures at depth, transition metals in outer-neritic shales could attain zero-valencies. Thus activated, in-reservoir catalytic oil-to-gas would commence. In this instance, the important factor for predicting oil or gas in reservoir rocks is the presence of ZVTM in sufficient concentrations to promote catalytic oil-to-gas. A rock assay specific to ZVTM in outcrop rocks, cuttings, or core samples would thus be a powerful exploration tool for reservoirs that either preserve oil (no ZVTM) or convert it to gas (with ZVTM).

Other than commonly assigned co-pending U.S. patent application Ser. No. 10/830,266, Applicant is unaware of any practical tests for trace amounts (i.e., ppb or less) of ZVTM in sedimentary rocks. Most rock methods use spectroscopic techniques, such as atomic absorption (AA) spectroscopy or inductively-coupled plasma atomic emission spectroscopy (ICP-AES), that do not differentiate between oxidation states. Nickel valency speciation has been achieved by X-ray absorption fine-structure spectroscopy using the National Synchrotron Light Source at Brookhaven National Laboratory (NY) and with anodic stripping voltammetry (Galbreath et al., "Chemical speciation of Nickel in residual oil ash," *Energy & Fuels,* 12:818–822, 1998), but the complexities of these methods preclude their use in routine rock analysis.

In addition to the above, a convenient assay for the direct determination of intrinsic paleocatalytic activity within sedimentary rock, for the purpose of making predictions in oil and gas exploration, would also be highly desirable. Applicant is unaware of any assays that measure the intrinsic catalytic activity of rocks to convert oil to gas under subsurface conditions.

BRIEF DESCRIPTION OF THE INVENTION

Embodiments of the present invention are generally directed to novel assays for measuring intrinsic paleocatalytic activities (k) of sedimentary rocks for converting oil to gas and projecting the activities to the subsurface based on the measured linear relationship between ln(k) and temperature (T). Sedimentary rocks sufficiently catalytic to convert 90+ % of their contained oil to gas at temperature T for oil residence time t are designated "gas habitats." Sedimentary rocks that cannot convert 90% of their oil to gas in time t are designated "oil habitats." Some embodiments of the present invention include approximating the intrinsic paleocatalytic activity k(T) of an un-drilled reservoir at temperature T from the linear relationship between ln k and T for a drilled reservoir rock that is genetically similar to the un-drilled reservoir rock. Some embodiments of the present invention enable the prediction of oil or gas in an un-drilled reservoir at temperature T for residence time t based on an approximation of its intrinsic paleocatalytic activity k(T) taken from the ln k vs T curve for a genetically related reservoir distal from the undrilled reservoir. Some embodiments of the present invention provide oil-gas habitat maps of stratigraphic rock units contouring the interface between oil and gas habitats based on the intrinsic paleocatalytic activities k(T) or their approximations at various locations in a basin. Some embodiments of the present invention enable prediction of the distribution of oil and gas in various reservoirs within a stratigraphic rock unit based on the oil-gas habitat map of that rock unit. Some embodiments of the present invention enable prediction of the distribution of oil and gas in various reservoirs in a stratigraphic rock unit proximal to a stratigraphic source rock unit within which oil and gas is generated and expelled into reservoirs within the proximal rock unit based on the oil-gas habitat map of the source rock unit. Some embodiments of the present invention enable the prediction of the conversion of oil to gas within a conduit rock along an oil migration pathway based on its intrinsic paleocatalytic activity k(T) or an approximation thereof at temperature T and the residence time t that migrating oil remains in the conduit.

Assays of the present invention typically comprise the following general steps: 1) processing rock sample potentially comprising zero-valent transition metal (ZVTM) so as to provide freshly exposed surface under conditions that preserve intrinsic catalytic activity; 2) exposing the rock sample to a mixture of hydrogen gas and hydrocarbon material under appropriate conditions such that the hydrocarbon material undergoes catalytic decomposition yielding catalytically-generated methane (CGM) if ZVTM is present; and 3) detecting the presence of any CGM. The presence of CGM confirms intrinsic catalytic activity imparted by ZVTM present in the sample. Generally, such rock samples are sedimentary rock samples, and processing (e.g., grinding) to provide freshly exposed surface is generally carried out in an inert, non-oxidizing atmosphere. Similarly, the exposure of such rock samples to hydrogen and hydrocarbon reactants is typically carried out in an inert, non-oxidizing atmosphere.

Depending on the embodiment, such above-described methane detection can provide qualitative and/or quantitative analysis of the sample. In some embodiments, when assaying a rock as described above, the qualitative analysis of catalytically-generated methane is sufficient to make predictive assessments as to the content. (i.e., primarily oil or primarily gas) of the reservoir from where the analyzed sample was extracted (source reservoir) or of any other reservoir that is genetically similar to the source reservoir. Two reservoirs are genetically similar if their overall organic and inorganic compositions are similar and if their genetic depositional environments are similar. In the Louisiana gas fields cited above, for example (Paine et al., "Geology of natural gas in South Louisiana," American Association of Petroleum Geologists, Memoir 9, Volume 1, Natural Gases of North America, Beebe, B. W., Editor, 376–581, 1968), the various reservoirs comprising interbedded sandstone and outer-neritic shales are genetically related, as defined here, for they share a common outer-neritic depositional environment. Outer-neritic environments include deposition along shelf breaks that are often highly reducing, organic rich sediments with high concentrations of transition metals (Cruickshank, M. J., and Roland, T. J. Jr., "Mineral deposits at the Shelfbreak," *SEPM* Special Publication No. 33, 429–436, 1983). Sandstone reservoirs interbedded with outer-neritic shale are not genetically similar to sandstone reservoirs interbedded with inner-neritic shale because outer-neritic and inner-neritic depositional environments are dissimilar, particularly with respect to metal concentrations and, therefore, their respective catalytic activities. In some or other embodiments, a more quantitative analysis provides greater insight into the content of such a source reservoir.

In some embodiments, upon quantitatively and/or qualitatively analyzing the catalytically-generated methane, the rock sample is ascribed an intrinsic catalytic activity. Such an intrinsic catalytic activity can then be projected onto the reservoir from where the sample was extracted (i.e., the source reservoir) or any other genetically similar reservoirs, to determine whether the intrinsic catalytic activity is sufficient to enable significant oil-to-gas conversion over geologic timescales and under environmental conditions within the reservoir. By processing the rock samples under inert conditions and exposing the processed rock samples to reactants under non-oxidizing conditions, the intrinsic catalytic activity so determined is equatable with the native catalytic activity in the reservoir.

Accordingly, the present invention, and the knowledge of catalytic activity gained thereby, is useful in predicting whether a particular reservoir will be likely to contain predominantly oil or predominantly gas.

In some embodiments, an analysis of the amount of methane produced under a given set of conditions and in a given timeframe generates a rate constant, k, for such a reaction at a particular reaction temperature. If such rate constants are determined for two or more such reaction temperatures, a linear plot of ln k versus T (ln k vs. T plot) can be generated. Such ln k vs. T plots can be extrapolated to yield a rate constant for the source reservoir that is indicative of its paleocatalytic activity. With such a source reservoir rate constant, it is possible to determine the extent and significance of oil-to-gas processes within said reservoir under sub-surface conditions over geologic timescales by integrating k dt over the temperature interval in the subsiding basin.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION OF THE INVENTION

Figure 1:
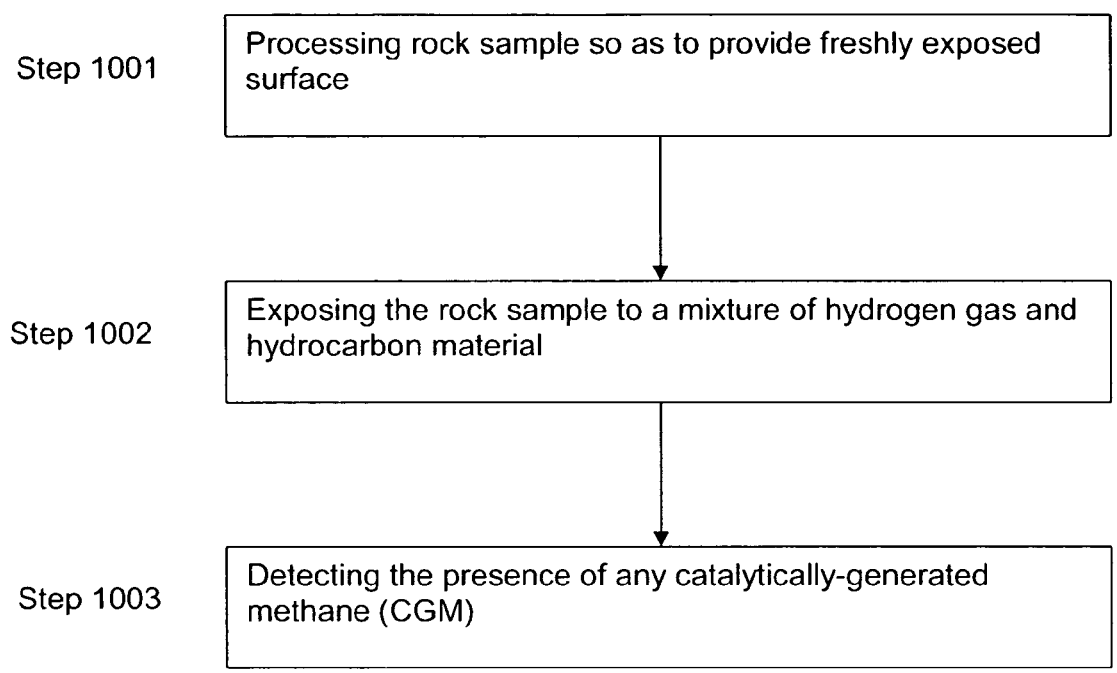
FIG. 1 is a flow diagram depicting the steps involved in a rock assay in accordance with embodiments of the present invention.

In the following description, specific details are set forth such as specific quantities, sizes, etc. so as to provide a thorough understanding of embodiments of the present invention. However, it will be apparent to those skilled in the art that the present invention may be practiced without such specific details. In many cases, details concerning such considerations and the like have been omitted inasmuch as such details are not necessary to obtain a complete understanding of the present invention and are within the skills of persons of ordinary skill in the relevant art.

Referring to the drawings in general, it will be understood that the illustrations are for the purpose of describing a particular embodiment of the invention and are not intended to limit the invention thereto.

The present invention concerns paleocatalysis, a new field concerning catalysis proceeding over geologic time. Because these reactions are orders of magnitude slower than traditional catalytic reactions, they present formidable analytical challenges. A typical sedimentary rock can have as little as parts-per-billion (ppb) levels of zero-valent transition metal (ZVTM) and be effective paleocatalysts in the subsurface. In contrast, typical industrial catalyst have metal concentrations in the parts-per-hundred range. Industrial catalytic reactions will take minutes where paleocatalytic reactions will take millions of years. The analytical challenge is this: a reservoir rock that converts oil to gas in two million years at 150° C., will generate only ~7×10$^{-7}$ g gas/(g rock hr) at 280° C. In one embodiment of the invention disclosed herein, this problem is addressed by sending 100% of the product (catalytic methane) directly into the analytical detector, typically a flame ionization detector (FID), to maximize accuracy and sensitivity. Using such techniques, it is possible to accurately measure paleoactivities as low as 10$^{-9}$ g gas/(g rock hr) at reasonable laboratory temperatures. In another embodiment of the invention, unusually stable light hydrocarbons (ethane and propane, for example) are used as reactants so that high-temperature assays can be employed to boost product yield without contaminating the product with thermal cracking products. The Applicant is unaware of other analytical procedures for determining paleocatalytic activities with this degree of sensitivity and accuracy. The Applicant is also unaware of other analytical procedures for determining intrinsic catalytic activities of reservoir rocks, activities that realistically project to subsurface activities under natural conditions. The Applicant is also unaware of methods for predicting oil or gas in various reservoirs based on their intrinsic catalytic activities.

While most of the terms used herein will be recognizable to those of skill in the art, the following definitions are nevertheless put forth to aid in the understanding of the present invention.

"Sedimentary rock," as defined herein, refers generally to rock formed by the accumulation and cementation of mineral grains transported by wind, water, or ice to the site of deposition or chemically precipitated at the depositional site. The sedimentary rocks specific to this invention include reservoir rocks, source rocks, and conduit rocks. Reservoir rocks are rocks that trap and sequester migrating fluids. "Source rocks" are rocks within which petroleum is generated and either expelled or retained. "Conduit rocks", as defined herein, are rocks through which petroleum migrates from its source to its final destination. A "sedimentary basin," as defined herein, is an accumulation of a large thickness of sediment, as in sedimentary rock. "Outcrop rocks," as defined herein, generally refers to segments of bedrock exposed to the atmosphere.

A "target reservoir", as defined herein, refers to a drilling prospect in a sedimentary basin comprising a sedimentary rock believed to be a reservoir containing economic quantities of oil or gas.

A "gas habitat," as defined herein, refers to a "sedimentary rock" within a sedimentary basin that is sufficiently catalytic to convert 90% or more of its contained oil to gas over the specified time-temperature residence interval, typically 10 million years (Ma) for basins where subsidence rates place reservoirs at temperature $T_r$ (±10° C.) for 10 Ma. The rate of oil-to-gas conversion at T, k(T), is determined from the linear ln k vs. T equation, like that shown in the plot of FIG. 5 determined for a rock from multiple rock assays at different temperatures. Alternatively, k(T) can be approximated from a single rock assay from the Arrhenius equation in Mango, "Transition metal catalysis in the generation of natural gas," *Organic Geochemistry*, 24:977–984, 1996, assuming Ni is equivalent to ZVTM. A temperature vs. time t plot, T vs log(Ma), like the "Ni Equivalent" curves in FIGS. 6 & 7, define the gas habitat field to the right of the temperature-time curve. These curves, or curves for genetically similar reservoir rocks, define where in time-temperature space a given rock will have a high probability of containing gas.

An "oil habitat," as defined herein, refers to a "sedimentary rock" within a sedimentary basin that is not sufficiently catalytic at a specified basin temperature T to convert 90% or more of its contained oil to gas over a specified period of geologic time t. The temperature-time curve for a specified rock defines the oil habitat field for that reservoir rock to the left of the curve. Thus, there is a high probability of finding gas in a reservoir targeted for drilling designated a "gas habitat" and oil in a reservoir targeted for drilling designated an "oil habitat." See commonly assigned co-pending U.S. patent application Ser. No. 10/830,266. Conversely, such ZVTM content can be inferred indirectly through a determination of intrinsic catalytic activity.

"Oil-to-gas," as defined herein, refers to geological processes in which crude oil (higher molecular weight hydrocarbons) converts into natural gas (lower molecular weight hydrocarbons). In the "thermal model," as defined herein, which is the generally accepted but imperfect model, oil-to-gas proceeds through thermal cracking and is thus a function of reservoir temperature and geologic time. Oil-to-gas in the "catalytic model," as defined herein, refers to a newer, but experimentally confirmed process, whereby oil is catalytically converted to gas with the aid of ZVTM. See Mango et al., "Role of transition-metal catalysis in the formation of natural gas," *Nature*, 368:536–538, 1994. The reservoir rock in the catalytic model is an active agent in oil-to-gas and a passive agent in the thermal model. Concentrations of ZVTM control oil-to-gas rates in the catalytic model and the kinetic parameters associated with thermal cracking control oil-to-gas rates in the thermal model. The two models have profoundly different predictive powers in oil and gas exploration.

An "active reservoir," as defined herein and in accordance with the oil-to-gas catalytic model, refers to a reservoir in which the surrounding sedimentary rock comprises at least a critical concentration of ZVTM as defined above. An "inactive reservoir," as defined herein and in accordance with the oil-to-gas catalytic model, refers to a reservoir with a less than critical concentration of ZVTM.

"Transition metal," as defined herein, refers to metals comprised of elements of the "d-block" of the Periodic Table. Specifically, these include elements 21–29 (scandium through copper), 39–47 (yttrium through silver), 57–79 (lanthanum through gold), and all known elements from 89 (actinium) on. Iron (Fe), cobalt (Co), and nickel (Ni) all have special relevance, however, due to their established catalytic activity. See Mango and Hightower, "The catalytic decomposition of petroleum into natural gas," *Geochimica et Cosmochimica Acta*, 61:5347–5350, 1997. "Zero-valent transition metal(s)," as used herein, are transition metals in their zero-oxidation (i.e., neutral) state.

"Quantitative analysis," as defined herein, generally refers to the determination of species quantity and/or concentration with a high level of precision. In contrast, "qualitative analysis" generally describes a lower level of precision, but still at a level capable of being used for predictive determinations.

An "assay," according to the present invention, generally refers to a quantitative or qualitative analysis (i.e., evaluation) of a sample. To assay a sample is to subject it to quantitative or qualitative analysis.

"Catalytically-generated methane," abbreviated "CGM" and as used herein, refers to methane generated via the catalytic decomposition of hydrocarbon material. Such catalytic decomposition, in the assays of the present invention, is induced via the catalytic activity of rock samples comprising ZVTM, and in accordance with the catalytic oil-to-gas model. Without such ZVTM present in the rock sample being assayed, no CGM will be produced.

"Catalytic activity," as defined herein, refers to the propensity of a catalyst to catalyze the catalytic decomposition of hydrocarbons to form CGM. "Intrinsic catalytic activity" refers to an unadulterated catalytic activity (i.e., such activity has not been compromised by exposure to oxygen) of a rock sample (source rock)) that is equitable to the native catalytic activity of the reservoir or reservoiric region from where the sample was extracted.

"Genetically similar," as defined herein, refers to rocks that are similar in overall organic and inorganic composition and which were deposited under similar depositional environments. Genetically similar rocks can be expected to contain similar concentrations of ZVTM and have similar levels of catalytic activity.

"Paleocatalysis," as defined herein, refers to catalytic reactions that proceed over geologic time. The paleocatalytic reaction specific to this invention is the conversion of oil to natural gas catalyzed by ZVTM. Like conventional commercial catalysts, paleocatalysts will express different levels of catalytic activity depending on how they were synthesized. Thus, one rock possessing ZVTM need not be similar in catalytic properties to another rock possessing similar concentrations of ZVTM. Genetically similar rocks, on the other hand, having been naturally synthesized under similar circumstances, should be similarly catalytic.

"Habitat maps," as defined herein, refers to maps of stratigraphic rock units showing the lines of intersection between oil and gas habitats as defined herein.

Embodiments of the present invention are generally directed to novel assays for ZVTM, and to methods of assaying rock samples potentially comprising ZVTM for intrinsic catalytic activity. The novel assays of the present invention are generally methods or processes for quantitatively and/or qualitatively evaluating the catalytic activity of, and the presence of ZVTM in, rock samples. Furthermore, application of such assays to oil and gas exploration provides for revolutionary advances in the predictability of oil and gas deposits based upon observed catalytic activity and/or the levels of ZVTM present in the surrounding sedimentary rock.

Referring to FIG. 1, assays of the present invention generally comprise the following steps: (Step 1001) processing rock sample potentially comprising ZVTM so as to provide freshly exposed surface; (Step 1002) exposing the rock sample to a mixture of hydrogen gas and hydrocarbon material (reaction mixture) under appropriate conditions such that the hydrocarbon material undergoes decomposition yielding catalytically-generated methane if ZVTM is present; and (Step 1003) detecting the presence of any catalytically-generated methane (CGM). The presence of CGM confirms intrinsic activity imparted by ZVTM in the sample. Generally, such rock samples are sedimentary rock samples. Typically, a heat extraction step is carried out between Steps 1001 and 1002 to extract from the sample any non-catalytically produced hydrocarbons (including methane) that could contaminate the final catalytically-generated methane (CGM) product. In some embodiments, a separating step is carried out between Steps 1002 and 1003, wherein CGM is separated from other hydrocarbons. Additionally, in some embodiments, the amount of CGM generated in Step 1002 is measured and quantified.

Typically, the rock sample is obtained from a reservoir of interest such that information about said rock, acquired through the assays of the present invention, is equatable to the reservoir itself (the source reservoir) and any other genetically similar reservoir. There is great flexibility in the quantity of rock sample used in the assays of the present invention. Generally, the amount of rock sample used is between about 0.1 g and about 20 g, typically between about 0.5 g and about 10 g, and more typically between about 0.5 g and about 5 g. In some embodiments, "side wall" rock samples are selected for the assay because such samples are less likely to be contaminated by oxygen. In some embodiments, outcrop rock are selected for the assay because such samples, if sufficiently large (a few mm in diameter), retain an inner core uncontaminated by oxidation.

Processing rock sample potentially comprising ZVTM so as to provide freshly exposed surface generally comprises a grinding technique, wherein the rock sample is ground. Such grinding can be accomplished with mortar and pestle by hand or mechanically milling by placing the rock samples in a closed brass cylinder containing a brass ball and shaking the cylinder with a mechanical 'paint shaker' for a short period of time, typically 15 minutes. Mechanical rock crushing in brass prevents sample contamination by transition metals in steel cylinders and balls. Because mechanical rock crushing can generate heat, and thus promote the oxidation of ZVTM if mechanical crushing is carried out in air, it is best to seal the cylinder in an inert atmosphere free of oxygen.

There can be considerable variability in the mesh size and surface area of the particles of which the ground rock sample is comprised. In some embodiments, the ground sample is sieved to include or exclude particles of a particular size or range of sizes.

Generally, the above-described processing to provide freshly exposed surface is generally carried out in an inert, non-oxidizing atmosphere. Suitable inert, non-oxidizing atmospheres include, but are not limited to, inert gases like Ar, He, $N_2$, Kr, and combinations thereof. In some embodiments, the inert gases are scrubbed of oxygen ($O_2$) by passage through a special filter. Such filters typically comprise metals which reacts with the $O_2$.

Care is generally taken to ensure that the processed samples do not contact $O_2$ until after they have been exposed to hydrogen/hydrocarbon in the assay reaction. If such processed samples do come into contact with $O_2$, any zero-valent metals potentially present in such samples will be at least partially oxidized, and any catalytic activity that the rock might possess will be reduced below the native catalytic activity. This is because the catalytic oil-to-gas process is highly specific to zero-valent metals and the active sites on the surfaces of zero-valent metals are extremely sensitive to destruction by oxygen. Such oxidation will lead to catalytic activity determinations for the rock sample that are below that for the source reservoir. Consequently, any projection of such determined activity onto the source reservoir will be underestimated.

Figure 2:
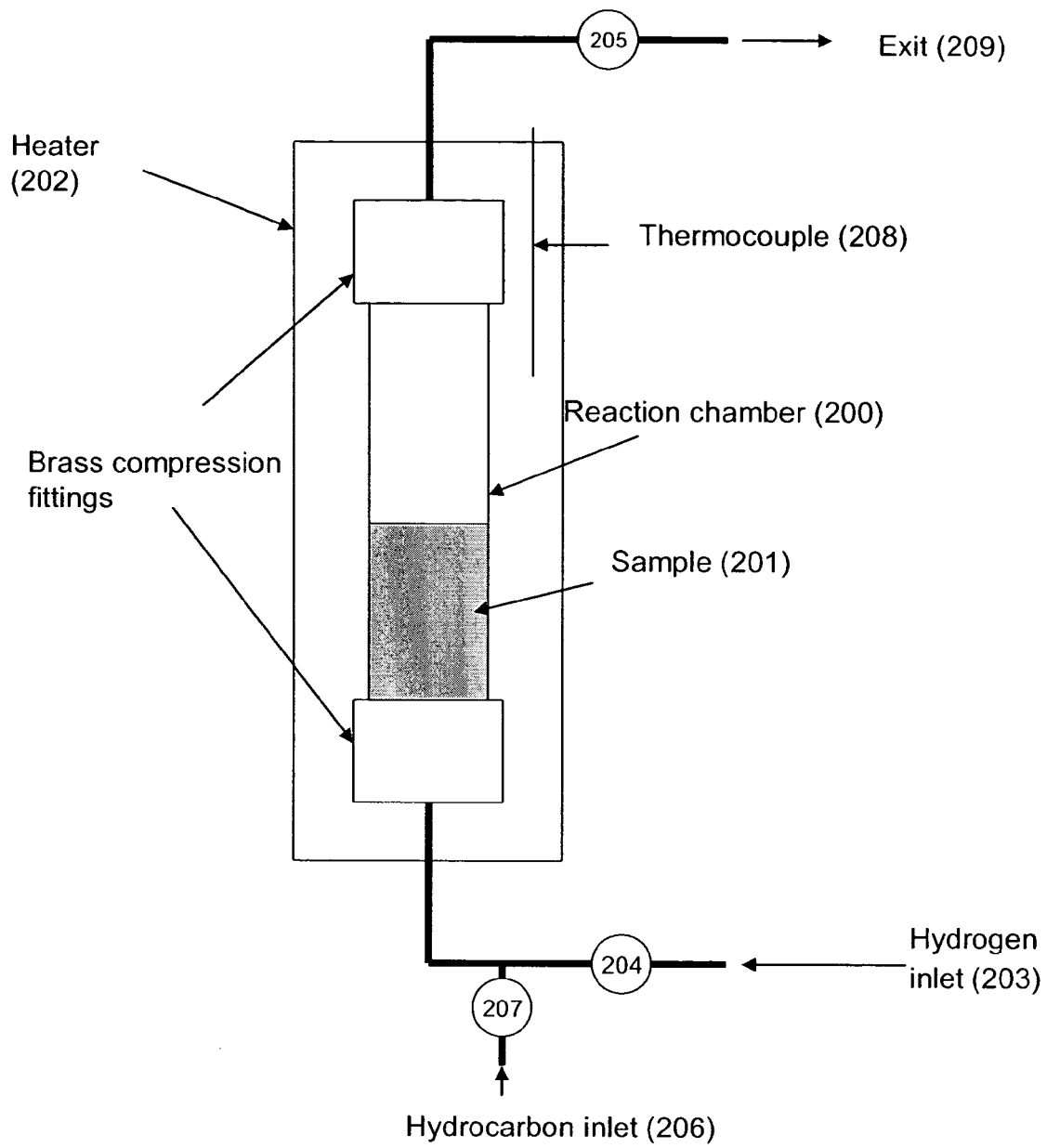
FIG. 2 depicts an exposure chamber, operable for both static and flow exposures, in accordance with some embodiments of the present invention.

The step of exposing can be carried out in either a static or flow system. Referring to FIG. 2, in an exemplary static system, a rock sample 201 is placed in a reaction chamber 200 capable of being heated with a heating element 202. Hydrogen reactant gas is introduced through inlet 203 with valve 204 open and valve 205 open. Hydrocarbon reactant is introduced through inlet 206 with valve 207 open. With sufficient reactants in the reaction chamber 200, the system is closed by closing valves 204, 205 and 207. The closed chamber is then heated to the desired level (determined via thermocouple 208). After sufficient time, valves 204 and 205 are opened allowing hydrogen gas to pass through the reaction chamber 200 carrying the product gases, potentially comprising CGM, out of the reaction chamber through exit 209 to a separator that removes CGM from all higher hydrocarbons and sends it to a detector for analysis. Alternatively, such a system could be run in a flow mode, wherein valves 204, 205, and 207 are kept open. Such flow scenarios, however, generally require detection techniques with greater sensitivity than that required for the static systems.

Exposure duration, i.e., the time in which a reaction mixture is in contact with a processed rock sample, can vary considerably. Generally, such exposure duration is between about 1 minute and about 30 days, typically between about 1 minute and about 24 hours, and more typically between about 1 minute and about 1 hour.

Exposure conditions include variables such as temperature and pressure. The temperature at which the step of exposing is carried out is generally between about 150° C. and about 450° C., typically between about 200° C. and about 350° C., and more typically between about 220° C. and about 300° C. The hydrogen gas partial pressure at which the step of exposing is carried out is generally between about 1 torr and about 100 torr, typically between about 1 torr and about 50 torr, and more typically between about 1 torr and about 5 torr. These temperatures are generally above that typically found in source reservoirs.

Typically, when exposing a rock sample to a mixture of hydrogen gas and hydrocarbon material, the hydrocarbon to hydrogen gas ratio can be between about 1:1000 and about 1000:1, as determinable by their partial pressures. Because this catalytic reaction is zero-order, its rate is independent of reactant concentrations beyond sufficient concentrations to saturate the active sites dispersed over the rock surface. Reactant concentrations (partial pressures of hydrogen and hydrocarbon) are, therefore, critical only below saturation concentrations. To obtain accurate assays, it is essential to maintain hydrogen and hydrocarbon concentrations above saturation. In some embodiments, one or both of the hydrocarbon material and hydrogen gas are optionally scrubbed of oxygen prior to being introduced into the reaction chamber. In some embodiments, the hydrocarbon material and hydrogen gas are pre-mixed prior to being introduced into the reaction chamber through inlet 207, while in other embodiments they are mixed within the reaction chamber by mixing the rock sample with hydrocarbon prior to placing the sample into the reaction chamber 200 or by injecting hydrogen through inlet 203 and hydrocarbon through inlet 206 separately.

The hydrocarbon material typically comprises one or more gaseous hydrocarbon species, but may also comprise liquid hydrocarbon material. In some embodiments, a quantity of a single hydrocarbon material is used, but mixtures of hydrocarbon species can also be employed. Typically, the hydrocarbon material comprises hydrocarbon species having between two and eighteen carbon atoms. Such hydrocarbon species can be aliphatic and/or aromatic and may contain one or more heteroatoms (e.g., O, N, S).

As mentioned above, in some embodiments, between the steps of exposing and detecting, a separating step is employed. Such separating steps can be used to separate any catalytically generated methane, potentially produced in the exposing step, from other hydrocarbon species. In some embodiments, this separation involves a cold trap (e.g., a liquid nitrogen trap) that condenses all other hydrocarbons, but allows methane to pass through and on to the detector/analyzer. In other embodiments, a chromatographic separation is employed. In such latter embodiments, a gas chromatographic column is usually employed, the column comprising any one of a number of suitable stationary phases suitable for the separation of methane from heavier hydrocarbons.

In some embodiments, detecting the presence of CGM in the above-described assay involves a detection device selected from the group consisting of a flame ionization detector (FID), a mass-selective detector, a spectroscopic detector, an electron capture detector, a thermal conductivity detector, a residual gas analyzer, and combinations thereof.

Depending on the embodiment, such above-described methane detection can provide qualitative and/or quantitative analysis. In some embodiments, when assaying a rock as described above, the qualitative analysis of catalytically-generated methane is sufficient to make predictive assessments as to the content (i.e., primarily oil or primarily gas) of a reservoir from where the analyzed rock was extracted. In some or other embodiments, a more quantitative analysis provides greater insight into the content of the source reservoir.

In some embodiments, oil or gas predictions can be made on a reservoir other than the source reservoir if the two reservoirs share a common depositional environment and thus can be expected to be similar in overall composition and ZVTM content. Such reservoirs are referred to here as "genetically similar" reservoirs. This application is particularly powerful because it can potentially predict oil or gas in an un-drilled reservoir based on analysis of rocks taken from drilled genetically similar reservoirs distal from the un-drilled reservoir. In other embodiments, stratigraphic units can be mapped for catalytic activity by assaying representative rock samples covering the various depositional environments throughout the stratigraphic units. From the paleo-catalytic activities at depth and residence times, habitat maps can be constructed showing where in these units oil will convert to gas and where it should not, thus where in the basin the probability for oil is high (oil habitats) and where it is low (gas habitats). Habitat maps could be particularly useful in mapping sedimentary rocks that are particularly rich in transition metals such as the outer-neritic shales (Cruickshank, M. J., and Roland, T. J. Jr., "Mineral deposits at the Shelfbreak," SEPM Special Publication No. 33, 429–436, 1983; Mann, U., and Stein, R. "Organic facies variations, source rock potential, and sea level changes in Cretaceous black shales of the Quebrada Ocal, Upper Magdalena Valley, Colombia," *American Association of Petroleum Geologists, Bulletin* 81:556–576, 1997) and the so-called black shales (Rimmer, S. M., "Geochemical paleoredox indicators in Devonian-Mississippian black shales, Central Appalachian Basin (USA)," *Chemical Geology* 206: 373–391, 2004.).

In some embodiments, upon quantitatively and/or qualitatively analyzing the catalytically-generated methane, the rock sample is ascribed an intrinsic catalytic activity. Such an intrinsic catalytic activity can then be projected onto the reservoir (from where the rock was extracted (i.e., the source reservoir), or a genetically similar reservoir, so as to determine whether the intrinsic catalytic activity is sufficient to enable significant oil-to-gas conversion over geologic timescales (e.g., eons) and under environmental conditions (temperatures and pressures) within the reservoir. By processing the rock samples under inert conditions, thereby precluding oxidation of the active sites in any ZVTM potentially present, the intrinsic catalytic activity so determined is equatable to the native activity within the reservoir.

The usefulness of many such above-described embodiments lies in using the knowledge of catalytic activity to predict whether a particular reservoir will be likely to contain predominantly oil or predominantly gas, based upon the catalytic activity of the reservoir, as determined from analyzing a rock sample obtained from said reservoir or a genetically similar reservoir, with an assay of the present invention. Such assays can permit the designation of a reservoir as being a gas habitat or an oil habitat, in accordance with the oil-to-gas model, with a direct measurement of the catalytic activity of source rock from said reservoir or from a genetically similar reservoir.

In some embodiments, an analysis of the amount of methane produced under a given set of conditions and a given timeframe permits the generation of a rate constant, k, for such a reaction for a particular reaction temperature. If such rate constants are determined for two or more such reaction temperatures, a plot of ln k versus T (ln k vs. T plot) can be generated. Such ln k vs. T plots can be extrapolated to yield a rate constant for the source reservoir or genetically similar reservoir. With such a source reservoir rate constant, it is possible to determine the extent and significance of oil-to-gas processes within said reservoir over geologic timescales.

Predictive determinations of oil or gas in a reservoir are based upon the required presence of ZVTM for catalytic conversion of heavier hydrocarbons to natural gas (Mango, "The origin of light hydrocarbon," *Geochimica et Cosmochimica Acta*, 64:1265–1277, 2000). For example, outer-neritic shales (black shales) are one of the richest sources of transition metals in sedimentary rocks, and reservoirs comprising such shales are much more likely to be active reservoirs, i.e., gas habitats as opposed to oil habitats. The present invention permits such predictive determinations to be made via direct evaluation of the intrinsic catalytic activity of source rock—as opposed to determining whether such rock has a threshold concentration of ZVTM.

While not intending to be bound by theory, it is believed that interaction of the reaction mixture is primarily a surface phenomenon. In such cases, the levels of potential catalytic activity, relative to the surface area and/or surface area per unit mass of the sample, can be quantified. An exemplary method of determining surface area is by Brunauer, Emmet, and Teller (BET) analysis.

In some embodiments, one or more of the above-described processes may comprise one or more contamination control measures, wherein such contamination control measures are employed when handling samples prior to or during the assay process.

The ZVTM of significance with respect to the methods and processes of the present invention include all ZVTM that suitably catalyze the decomposition of hydrocarbons to yield catalytically-generated methane in accordance with the methods and processes of the present invention. For the purposes of oil and gas exploration, these include, but are not limited to, iron (Fe), cobalt (Co), and nickel (Ni).

While the discussions herein have focused primarily on catalytic activity afforded by ZVTM, the present invention is generally directed toward ascertaining intrinsic catalytic activity of rock samples for the purpose of ascertaining catalytic oil-to-gas conversion within reservoirs. As such, Applicant does not preclude the possibility that zero-valent metals other than transition metals may provide some catalytic activity. Thus, it is possible that rare earth metals, in their zero-valent state, can contribute to the oil-to-gas conversion, even if such contribution is small by virtue of their presence in trace amounts.

In some embodiments, the optional step of separating is coupled with the detection/analysis step. This is particularly well suited for embodiments employing chromatographic separation, and to gas chromatographic separations in particular. Suitable gas chromatographic (GC) methods, coupled with a detection/analysis technique, include, but are not limited to, gas chromatography-mass spectrometry (GC-MS), gas chromataography-electron capture detection (GC-ECD), gas chromatography-pulsed flame photometric detection (GC-PFPC), gas chromatography-Fourier transform infrared spectroscopy detection (GC-FTIR), and combinations thereof.

Most generally, the present invention is directed to methods of making predictive determinations whether a reservoir is active or inactive, in accordance with the oil-to-gas catalytic model, by assaying the surrounding sedimentary rock for catalytic activity, and by consequence, ZVTM.

In economic terms, if a reservoir is sufficiently removed from natural gas markets, then the economic incentives for drilling in an oil habitat greatly outweigh those for drilling in a gas habitat. The present invention permits such determinations to be made inexpensively with a relatively high level of accuracy, helping to avoid significant and costly exploration processes in order to ascertain the reservoiric content.

The following Examples are provided to demonstrate particular embodiments of the present invention. It should be appreciated by those of skill in the art that the methods disclosed in the Examples which follows merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

This Example serves to illustrate an embodiment by which the present invention can be used to assay sedimentary rock for oil-to-gas catalytic activity via the detection of catalytically-generated methane produced when a gaseous hydrocarbon species is contacted with said rock in the presence of hydrogen and under static exposure conditions.

A one gram sample of source rock (Miocene Monterey formation, California, taken from an outcrop on Venice Beach) was ground to 60 mesh and mixed with 5 cubic centimeters (cc) of sand under argon, and then heat-extracted at 300° C. for 30 minutes in flowing purified $H_2$. Referring to reaction system 300 in FIG. 3, this mixture was sealed in a 10 cc brass reactor 301, then pressure vented five times at room temperature with a gas mixture of 97% $H_2$ and 3% propane (C3), the gases purified by passage through commercial $O_2$ scrubbers 302 (BOT-2 purchased from Agilent Technologies, Willington, Del.). Each pressure vent involved opening 3-way valve 303 to vent. With valve 304 closed, the reactor was then pressurized to 50 psig with the gas mixture (valve 305 open), then closed by closing valve 306. With valve 306 closed, valve 304 was opened slowly to allow the reactor to vent to atmospheric pressure. This was repeated five times to remove all oxygen from the sample particles, the reactor 301, and all associated tubing. Inside the closed reactor at 50 psig gas mixture (valves 306 & 307 closed), a mixture of rock sample, hydrogen, and propane, the hydrogen and propane above catalyst saturation partial pressures, was then heated to 260° C. for 30 minutes, then brought back to room temperature. With the reactor at 200° C., it was then opened (valves 306 & 307 open) to flowing $H_2$ gas (valve 305 closed and valve 308 opened) through a liquid nitrogen ($LN_2$) trap 309 and directly into a FID detector 310 (3-way valve 303 open to FID) at a flow rate of ~0.2 cc/min (adjusted via needle valve 311), the same rate used to calibrate the detector using a 3% propane/hydrogen mixture as a standard for calculating g $CH_4$/pA sec (pA=pico amperes). An integrator attached to the FID detector integrated the eluting methane signal which indicated a rock activity of ~$3 \times 10^{-5}$ g $CH_4$/(g rock hr).

EXAMPLE 2

This Example serves to illustrate an embodiment wherein the hydrocarbon material is a liquid and illustrates activity suppression by high concentrations of hydrocarbon and also illustrates the catalytic nature of the reaction.

A sample of Monterey rock (0.88 g) like that in Example 1, heat-extracted at 350° C. for 30 minutes in purified $H_2$, was saturated with 100 micro liters of n-nonane (C9) and placed in Reactor 301. After five pressure-vents, as described in Example 1 using ultra pure $H_2$ purified through oxygen scrubber 302 at room temperature, the reactor was closed (valves 306 and 307 closed) and heated to 240° C. for 30 minutes. The product, vented to FID (310) at 100° C. over about 30 minutes, indicated a catalytic activity of ~$3 \times 10^{-6}$ g $CH_4$/(g rock hr). The reaction was repeated without adding additional n-nonane. The second product was ~70 times that of the first with an activity of ~$2 \times 10^{-4}$ g $CH_4$/(g rock hr). These results illustrate activity suppression in the first reaction by excess liquid hydrocarbon suppressing hydrogen diffusion to the active sites. Similar suppressions were observed for pure nickel powder when a film of wax was dispersed over its surface. Because excess hydrocarbon was removed between the first and second reaction on venting to FID (310), hydrogen access to the active sites was unimpeded in the second reaction. The dramatic increase in methane yield between the first and second reactions also illustrates the catalytic nature of the reaction. If thermal cracking were the source of methane, the yield in the first reaction would be greater than that in the second, not less.

EXAMPLE 3

This Example serves to illustrate an embodiment wherein the products are separated by gas chromatography. It also illustrates 1) that sedimentary rocks are catalytic in their natural state without added hydrogen or hydrocarbon, 2) that catalytic activity increases by a factor of 20 with $H_2$ addition, 3) that catalytic activity is destroyed with the addition of oxygen-contaminated 1% pentane/hydrogen, and 4) that hydrocarbons in a natural source rock (and pentane) undergo insignificant thermal decomposition to thermal methane under reaction conditions. These results illustrate that sedimentary rocks are naturally catalytic in the conversion of hydrocarbons to natural gas.

Figure 4:
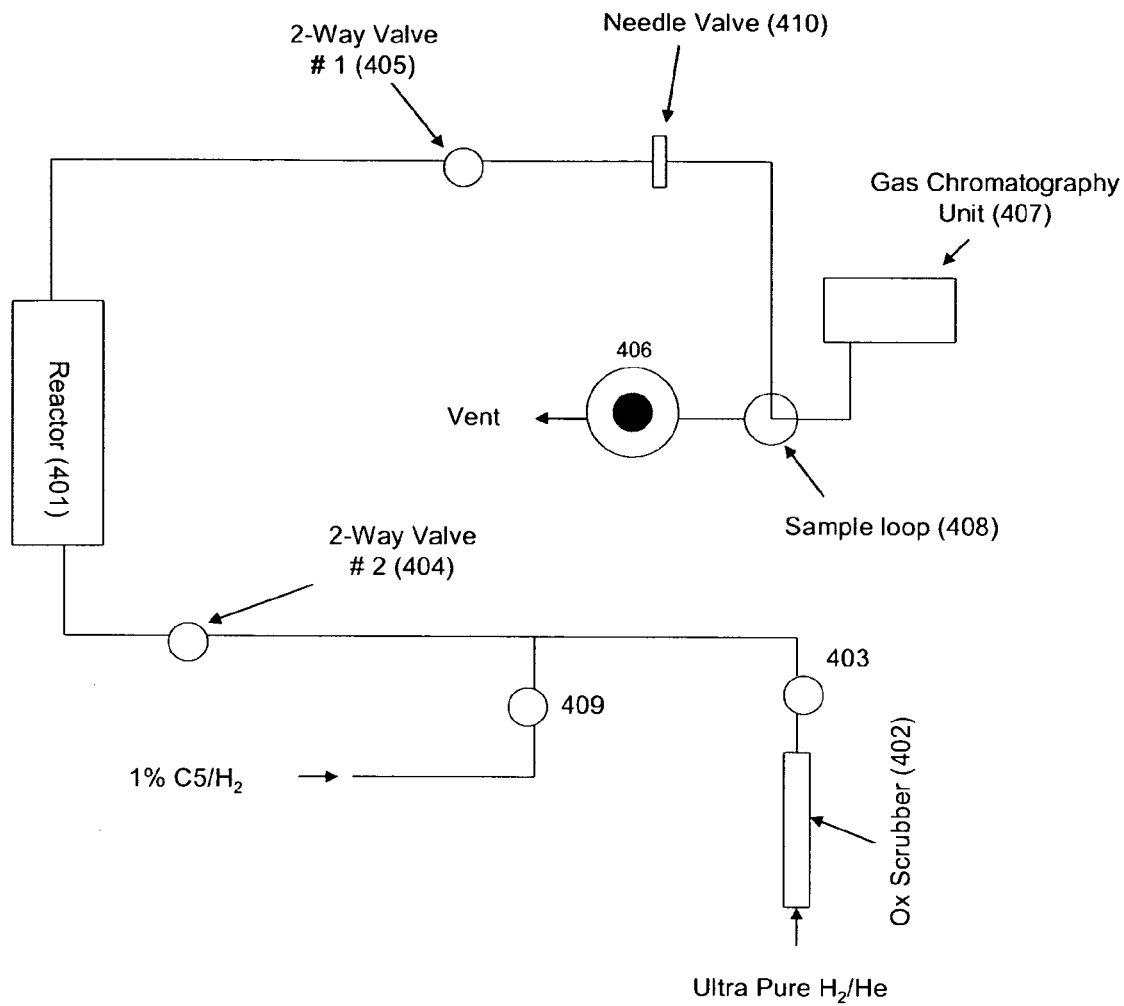
FIG. 4 depicts another reaction system in accordance with some embodiments of the present invention.

Referring to FIG. 4, a Monterey source rock similar to those used above (0.25 g), except that it was not heat-extracted, was placed in reactor 401 and flushed with purified He (through oxygen scrubber 402) to vent (valves 403, 404, 405, and 406 open) as the reactor temperature was increased from room temperature to 280° C. Reactor 401 was then closed (valves 404 and 405 closed) for 23 hours. Opened to He flow (280° C.) (valves 404 and 405 opened), 100 micro liter aliquots were taken at time intervals selected to capture maximum product from the effluent stream and sent to the GC unit 407 through sample loop 408 for product separation and analysis. A typical product was 69% methane (wt % C1–C4) with a methane GC peak intensity of 43 pA sec. The above reaction was repeated (0.3 g rock) using purified $H_2$ (through scrubber 402) in place of He. The product extracted from the effluent stream and analyzed under the same conditions showed significantly higher concentrations of methane: 350 pA sec. The composition of the product gas, corrected for olefins (thermal products), was 97% methane (C1–C4). A third reaction on the Monterey source rock under the same conditions except that the purified $H_2$ was replaced by a mixture of unpurified pentane (1%) in hydrogen (99%) (valve 409 open, valve 403 closed) showed only trace amounts of methane. This third reaction serves as a blank experiment in which the catalytic activity of the Monterey rock was destroyed by the unpurified gas. The experiment demonstrates that hydrocarbons (in the Monterey source rock and pentane) undergo minimal thermal decomposition to methane under these reaction conditions. Thus, the methane produced under the same conditions using purified gases was catalytic methane.

EXAMPLE 4

This Example serves to illustrate how a ln k vs. T plot can be generated and how such a plot can be extrapolated to yield k for reservoiric conditions.

Figure 3:
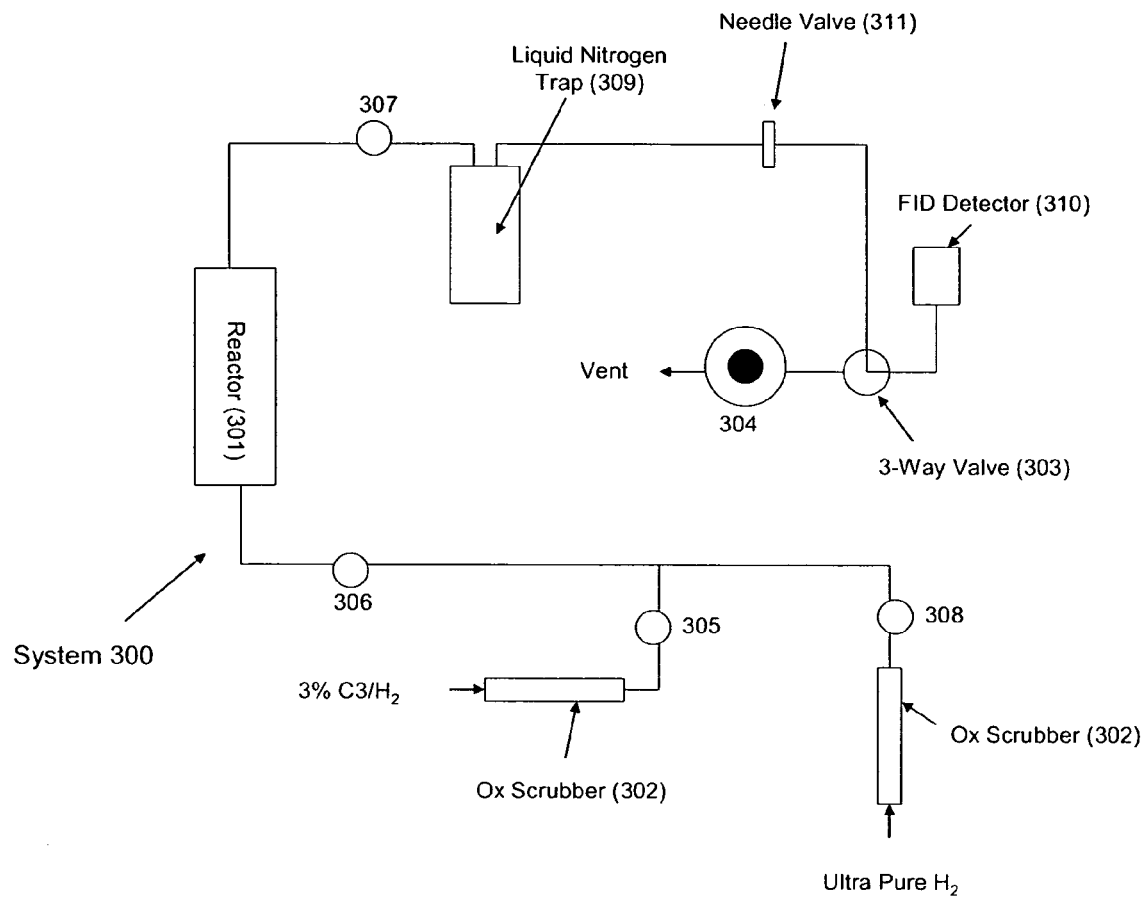
FIG. 3 depicts a reaction system in accordance with some embodiments of the present invention.
Figure 5:
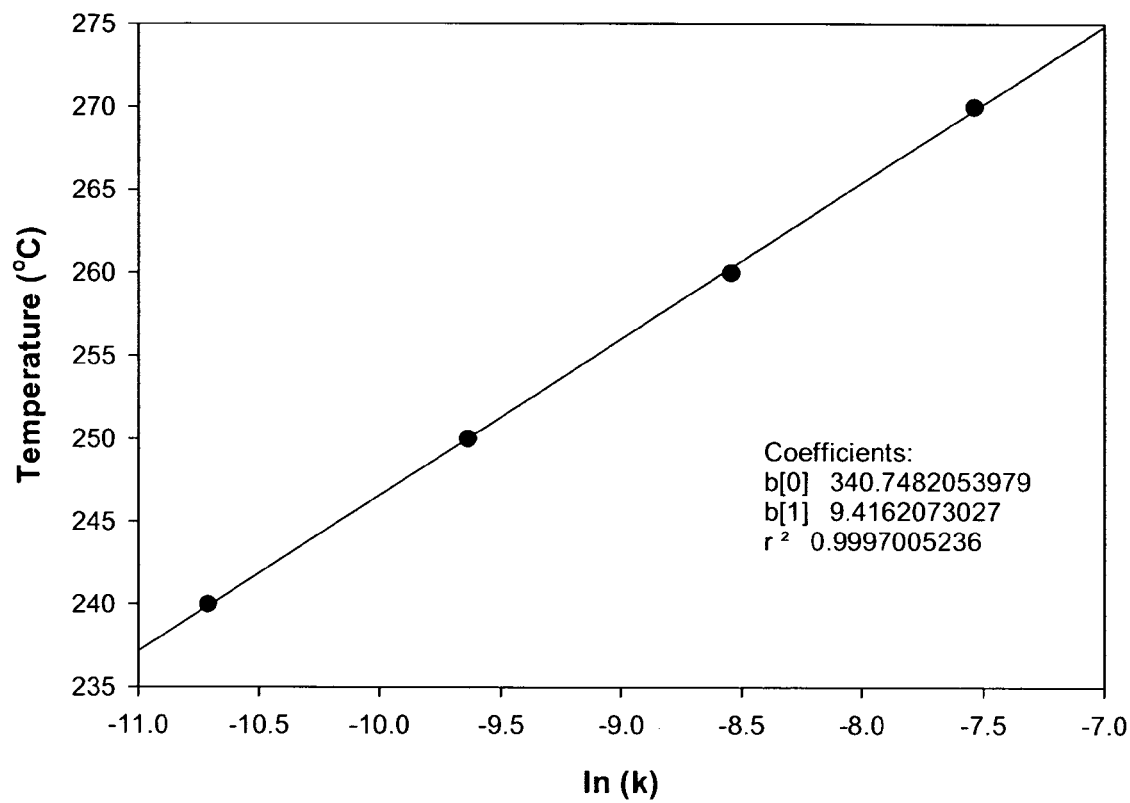
FIG. 5 is a ln(k) vs. T curve generated in accordance with some embodiments of the present invention.

Steady-state flow reactions were carried out using ultra-pure nickel powder (~1 g) obtained from Sigma-Aldrich, 203904-25 (99.99% Ni), 100 mesh. 1% n-Pentane in $H_2$ was passed through the oxygen scrubber 302 in FIG. 3 at a flow rate of 0.4 cc/sec directly to FID detector 310 (valves 305, 306, and 307 open and 3-way valve 303 directed to detector 310). The methane signal (pA) climbed smoothly from 240 to 270° C. The plot in FIG. 5 shows a perfect linearity between ln k vs. T, where k was calculated from a prior calibration using 3% $C3/H_2$ ($k=(pA) \times 4.077 \times 10^{-11}$). The linearity in ln k vs. T and the independence between k and hydrogen and hydrocarbon concentrations (demonstrated in separate experiments) is consistent with zero-order kinetics.

EXAMPLE 5

This Example serves to illustrate an embodiment wherein the hydrocarbon material is a liquid dispersed on sand. It further illustrates an embodiment wherein the analysis of a rock from one basin correctly predicts gas in a genetically similar rock in an adjacent basin. A thermal cracking model incorrectly predicts oil.

n-Nonane (C9) was dispersed on pure quartz sand by evaporating to dryness a slurry of 100 cc sand and 50 ml pentane containing 1 g n-nonane. A sidewall core sample of Barnett shale (Mississippian) from the Hardeman basin, Texas was ground to 60 mesh under Ar and heat-extracted at 350° C. in flowing purified $H_2$ for 30 minutes. The product (0.84 g) was mixed with 5 cc of the nonane-impregnated sand and the mixture placed in Reactor 301 (FIG. 3). The reactor was pressure-vented (50 psig) with ultra pure $H_2$ as described above. With the reactor closed at room temperature and 50 psig $H_2$ (valves 306 & 307 closed), the reactor was heated to 280° C. for 1 hour, then cooled to 200° C., then opened to FID unit 310 through valve 303 by opening valves 306 and 307. The integrated methane product indicated a rate constant $k=\sim 1 \times 10^{-4}$ g $CH_4$/(g rock hr).

EXAMPLE 6

This Example serves to illustrate an embodiment wherein the reaction is carried out under static conditions from steady-state flow at constant temperature. It further illustrates the embodiment wherein unusually stable light hydrocarbons are employed as reactants so that high-temperature assays (350+° C.) can be employed to boost reaction rates without contaminating the catalytic methane with thermal cracking methane. Propane, used in EXAMPLE 6, has a half-life at 200° C. of 800 million years (Laidler, K. J., Sagert, N. H., and Wojciechowske, B. W. "Kinetics and Mechanisms of the thermal decomposition of propane," *Proceedings of the Royal Society* A270, 242–253, 1962) while ethane has a half-life of 50 billion years at the same temperature (Laidler, K. J., and Wojciechowske, B. W. "Kinetics and Mechanisms of the thermal decomposition of ethane," *Proceedings of the Royal Society* A260, 91–102, 1961). Cycloalkanes are also unusually stable and can be employed for high-temperature assays without contaminating the catalytic methane product with thermal methane (Mango, F. D., "The origin of light cycloalkanes in petroleum," *Geochim. Cosmochim. Acta* 54, 23–27, 1990). This further illustrates an embodiment wherein a rock from one basin correctly predicts gas in a genetically similar rock in the same basin.

A sample (4.6 gm) of Barnett shale core (Ft Worth basin, Sims-2 well) ground to 60 mesh under Ar was placed in reactor 301 (FIG. 3), pressure-vented 5 times with 50 psig pure $H_2$ (oxygen-scrubbed through 302), then heat-extracted under purified $H_2$ flow (0.2 cc/sec) for 30 minutes at 350° C. The inlet gas was then switched to 3% propane in hydrogen (purified through 302) by closing valve 308 and opening valve 305. Gas flow to FID (0.2 cc/sec) was then continued at 350° C. until the FID signal was constant, whereupon the reactor was closed (valves 306 and 307 closed) for 5 minutes, then opened to FID. A catalytic methane peak emerged after about 10 minutes: $A=1.03 \times 10^5$ pA sec, corresponding to a catalytic activity of $k(350° C.)=1.1 \times 10^{-5}$ g C1/(g rock hr). This rock would have a nickel-equivalent activity of $2.46 \times 10^{-13}$ g C1/(g rock hr) at 160° C. and would convert oil to gas in 6 Ma at this temperature (3% porosity filled with oil). Since the Barnett shale was at 160° C. for 20 Ma, genetically similar facies of Barnett shale would be designated gas habitats. After destroying all catalytic activity by injecting ~1 cc air with gas flow at temperature, a repeat of the reaction with 3% propane, 350° C., five minutes closed, showed no detectable amounts of methane, demonstrating the feasibility of high-temperature assay uncontaminated by thermal cracking.

Figure 6:
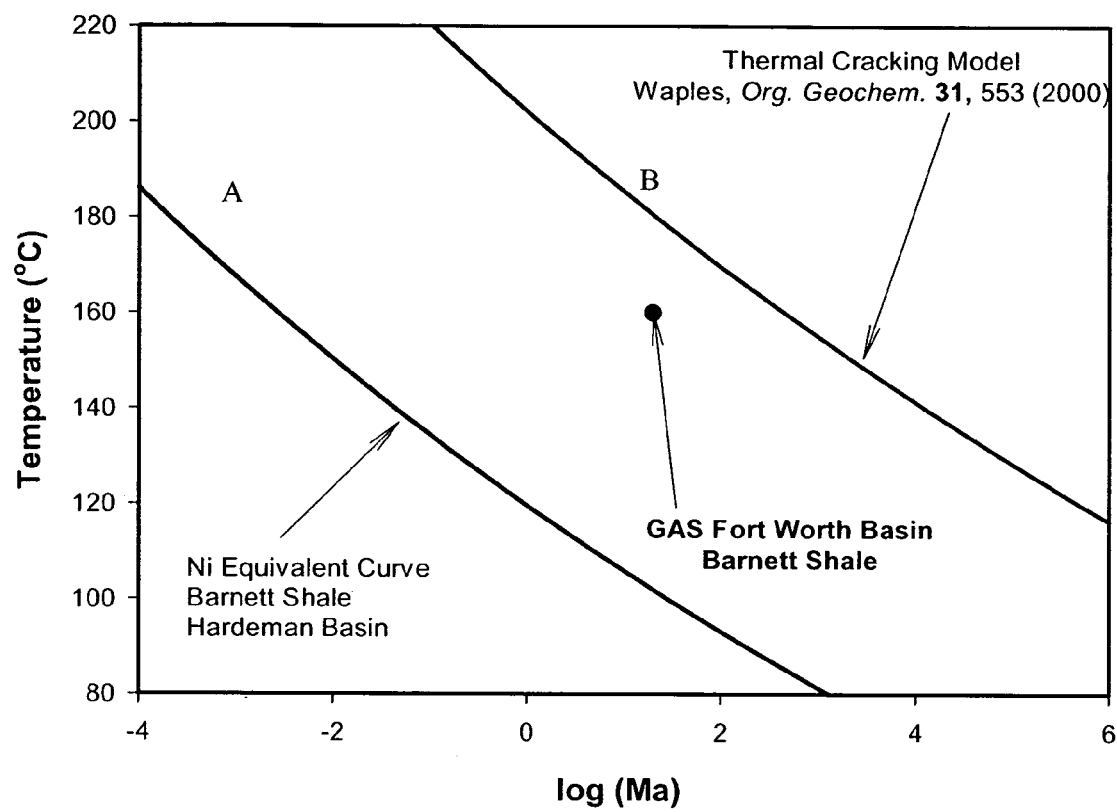
FIG. 6 is a plot of an application in which gas is correctly predicted in one basin based on a rock assay from a genetically similar reservoir rock from a different basin in accordance with some embodiments of the present invention.

FIG. 6 is a plot of temperature vs. residence time (in million of years, Ma) for the Barnett shale analyzed above (Example 5) showing where in time-temperature space this reservoir will contain oil (to the left of the Barnett curve, Curve A) and where it will contain gas (to the right of Curve A). The x axis is the log time, in millions of years (Ma), for 100% conversion of oil to gas in a rock with 3% porosity filled with oil (~0.013 g oil/g rock) at the indicated temperatures. Curve A, the Barnett curve (the 'Ni Equivalent Curve'), was constructed from the kinetic equation published by Mango (Mango, "Transition metal catalysis in the generation of natural gas," *Org. Geochem.* 24:977–984, 1996) for zero-valent nickel. A rate constant for Barnett at each temperature T ($k_T$) was calculated from the following equation, where k' is the rate constant for Ni published by Mango and $k_T$ is the 'nickel-quivalent' rate constant for Barnett: $k_T=(k'_T/k'_{280})\times 1E-04$. This curve is only an approximation of the true Barnett T vs time curve which is best constructed from multiple assays at multiple temperatures to obtain an adequate linear relationship between ln k and T. It should be stressed that any 'true' Barnett curve thus obtained would need calibration to natural conditions where lower hydrogen partial pressures and retained hydrocarbons would serve to suppress the intrinsic activities measured in assays. Curve B, the thermal cracking curve, was constructed from the oil cracking kinetic data published by Waples for the same 3% porosity rock (Waples, D. W., "The kinetics of in-reservoir oil destruction and gas formation: constraints from experimental and empirical data, and from thermodynamics," *Org. Geochem.* 31:553–575, 2000). The data point represents the gas deposits in the Mississippian Barnett shale in the Ft Worth basin, Tex. with an estimated residence time of 20 Ma at a temperature of ~160° C. A thermal cracking model based on the Waples curve will incorrectly predict oil in the Ft Worth basin while the Barnett curve, from a rock assay of Barnett shale in a genetically similar reservoir in an adjacent basin (Hardeman basin), correctly predicts gas.

Figure 7:
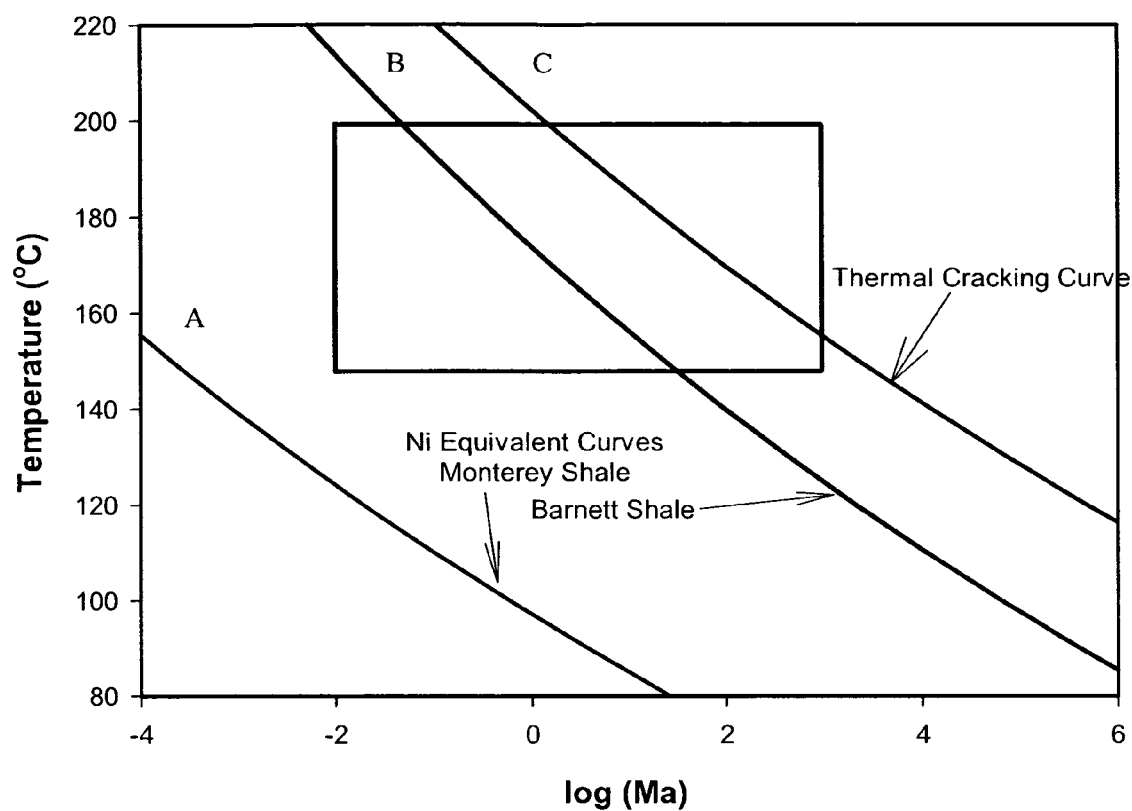
FIG. 7 is a plot of the differences between thermal cracking and the current invention in their capacities to explain oil-to-gas as seen in sedimentary basins.

The box in FIG. 7 encloses the time-temperature region where most oil-to-gas occurs in sedimentary basins according Hunt (Hunt, *Petroleum Geochemistry and Geology*, $2^{nd}$ ed., W. H. Freeman, New York, Chapter 7, 1996). Thus, any method for predicting gas must be effective in this time-temperature region. The thermal cracking model published by Waples (Waples, "The kinetics of in-reservoir oil destruction and gas formation: constraints from experimental and empirical data, and from thermodynamics," *Organic Geochemistry*, 31:553–575, 2000), which is typical of most such models, can explain only ~30% of the observed cases. The catalytic model, as reflected in rock assays on Barnett and Monterey rocks described herein, will predict gas throughout the critical zone.

Figure 8:
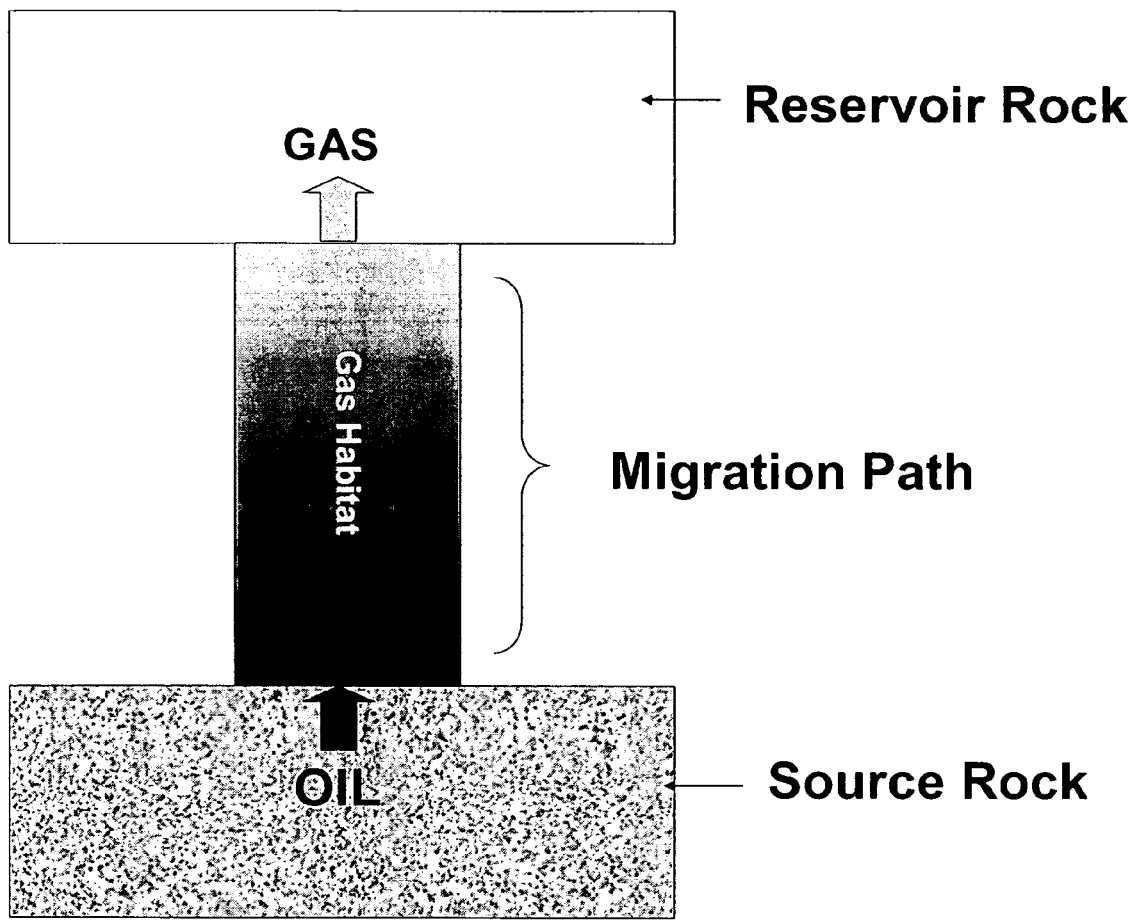
FIG. 8 illustrates a scenario wherein oil converts to gas while migrating from source rock to reservoir rock through conduits constituting gas habitats.

FIG. 8 illustrates another application of the invention where oil converts to gas while migrating from source rock to reservoir rock through conduits constituting gas habitats. Consider, for reference, the examples of oil-to-gas reported by Paine (Paine et al., "Geology of natural gas in South Louisiana," American Association of Petroleum Geologists, Memoir 9, Volume 1, Natural Gases of North America, Beebe, B. W., Editor, 376–581, 1968) in the giant gas fields in southern Louisiana occurring in sandstone reservoirs interbedded with outer-neritic shales at depths usually greater than 10,000 ft. (temperatures >140° C.). Outer-neritic shales tend to be rich in transition metals like the Monterey source rock analyzed herein. The Monterey rock exhibits robust activity in assay which projects to very high paleoactivities at the temperatures indicated in the Paine publication (see FIG. 7). At 160° C., for example, a sandstone reservoir interbedded with 1% Monterey shale would be a gas habitat at all residence times greater than 5,000 years—a tiny slice of geologic time. Migrating oil with a residence time greater than 5,000 years, at temperatures ~160° C., would be converted to gas as indicated in FIG. 8. This concept, the conversion of oil to gas in migration, is new to oil and gas exploration. It provides a potentially powerful explanation for how oil from one reservoir (an oil habitat) becomes gas in a shallower reservoir, also an oil habitat. Gas habitats along migration pathways constitute gas conduits in an otherwise all oil plumbing system.

Thus, in light of the foregoing, the present invention provides extremely sensitive assays for determining the catalytic activity of sedimentary rocks at levels as low as 0.01 μg $CH_4$/(g rock hr) based upon any ZVTM-induced catalytic decomposition of hydrocarbon material to generate methane. The fact that this activity is destroyed by oxygen points to a low valent-specific catalyst. That the catalytic action of pure zero-valent nickel is similarly destroyed by oxygen indicates that low-valent metals dispersed on the rock's surface are the active agents in sedimentary rocks. Furthermore, such catalytically-generated methane, if present, is indicative of the intrinsic catalytic activity of the rock sample. Assays at different temperatures yield a linear activity curve (ln k vs T) that is useful in predicting activities k at subsurface temperatures. Because subsurface conditions are different from laboratory conditions (hydrogen partial pressures, hydrocarbon concentrations and other unanticipated factors that might alter reaction rates) the activity curve should be calibrated on reservoirs for which residence time t, temperature T, and % oil conversion to gas are known, thus giving subsurface activity at temperature T, $k_s(T)$. A correction factor α ($\alpha=k_s(T)/k(T)$) thus converts the assay activity curve to the sub-surface curve: ln $k_s$ vs. T. Such curves give the rate constants for source reservoirs and all genetically similar non-source reservoirs at all subsurface temperatures. The time for 90+ % oil conversion to gas can then be calculated for all sub-surface temperatures. This yields a curve like the Ni equivalent curve in FIG. 6 that divides temperature-time space into oil and gas habitats, regions where the subject reservoirs have a high probability of containing oil or gas, respectively.

Thus, in light of the foregoing, the present invention provides extremely sensitive assays for determining the catalytic activity of rock samples based upon any ZVTM-induced catalytic decomposition of hydrocarbon material to generate-methane (e.g., in parts-per-billion quantities). Such catalytically-generated methane is unequivocal evidence of zero-valent metals dispersed on the rock's surface. Furthermore, such catalytically-generated methane, if present, is indicative of the intrinsic catalytic activity of the rock sample, and via projection, the source reservoir All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method comprising:
   a) a sample preparation step for exposing fresh surface of a quantity of rock sample potentially comprising zero-valent transition metal, wherein the sample preparation step is carried out under inert conditions;
   b) a reaction step for exposing the rock sample to hydrogen gas and a hydrocarbon material in an exposure environment, wherein said exposure leads to the catalytic generation of methane gas if zero-valent transition metal is present within the rock sample, and wherein the sedimentary rock sample, after undergoing the sample preparation step, is not exposed to $O_2$ until after the reaction step; and c) a detection step for detecting the presence of methane catalytically-generated by zero-valent transition metal potentially present in said rock sample.

2. The method of claim 1, wherein the sample preparation step involves a grinding process for exposing fresh surface of a quantity of rock sample potentially comprising zero-valent transition metal.

3. The method of claim 1, wherein the inert conditions comprise an atmosphere of inert gas, the gas having been scrubbed of oxygen.

4. The method of claim 1, wherein the reaction step comprises a duration of between about 1 minute and about 30 days.

5. The method of claim 1, wherein the reaction step comprises a duration of between about 1 minute and about 24 hours.

6. The method of claim 1, wherein the reaction step comprises a temperature of between about 200° C. and about 450° C.

7. The method of claim 1, wherein the reaction step comprises a hydrogen partial pressure of between about 0.1 torr and about 500 torr.

8. The method of claim 1, wherein the exposure environment of the reaction step is static.

9. The method of claim 1, wherein the exposure environment of the reaction step comprises a flow system.

10. The method of claim 1, wherein the mass ratio of hydrocarbon material to hydrogen used in the reaction step is between about 1:1000 and about 1000:1 prior to any potential catalytic decomposition of the hydrocarbon material.

11. The method of claim 1, wherein the hydrocarbon material introduced in the reaction step comprises hydrocarbon species having 2–25 carbon atoms.

12. The method of claim 1, wherein the hydrocarbon material introduced in the reaction step comprises hydrocarbon species possessing heteroatoms.

13. The method of claim 1, further comprising a separation step for separating any catalytically-generated methane from any other hydrocarbon species potentially present after the reaction step.

14. The method of claim 13, wherein the separating is done by condensing the other hydrocarbon species on a cold trap.

15. The method of claim 13, wherein the separating is done via chromatographic means.

16. The method of claim 1, wherein detecting the presence of catalytically-generated methane in the detection step involves a detection device selected from the group consisting of a flame ionization detector, a mass-selective detector, a spectroscopic detector, an electron capture detector, a thermal conductivity detector, a residual gas analyzer, and combinations thereof.

17. A rock assay comprising:
a) a sample preparation step for exposing fresh surface of a quantity of sedimentary rock sample potentially comprising zero-valent transition metal, wherein the sample preparation step is carried out under inert conditions;
b) a reaction step for exposing the sedimentary rock sample to hydrogen gas and a hydrocarbon material in an exposure environment under assay exposure conditions, the hydrocarbon material comprising hydrocarbon species having two or more carbons and wherein said exposure leads to the catalytic generation of methane gas if zero-valent transition metal is present within the sedimentary rock sample, and wherein the sedimentary rock sample, after undergoing the sample preparation step, is not exposed to $O_2$ until after the reaction step; and
c) an analysis step for ascertaining the presence of methane catalytically-generated by zero-valent transition metal potentially present in said rock sample and, if present, for ascribing an intrinsic catalytic activity to said sedimentary rock.

18. The rock assay of claim 17, wherein the sample preparation step involves a grinding process for exposing fresh surface of a quantity of rock sample potentially comprising zero-valent transition metal.

19. The rock assay of claim 17, wherein the exposure environment of the reaction step is static.

20. The rock assay of claim 17, wherein the exposure environment of the reaction step comprises a flow system.

21. The rock assay of claim 17, wherein the assay exposure conditions comprise a temperature of between about 200° C. and about 450° C.

22. The rock assay of claim 17, wherein the assay exposure conditions comprise a hydrogen partial pressure of between about 0.1 torr and about 500 torr.

23. The rock assay of claim 17, wherein the reaction step comprises a duration of between about 1 minute and about 30 days.

24. The rock assay of claim 17, wherein the mass ratio of hydrocarbon material to hydrogen introduced in the reaction step is between about 1:1000 and about 1000:1, prior to any potential catalytic decomposition of the hydrocarbon material.

25. The rock assay of claim 17, wherein the hydrocarbon material used in the reaction step comprises hydrocarbon species having 2–25 carbon atoms.

26. The rock assay of claim 17, wherein the hydrocarbon material used in the reaction step comprises hydrocarbon species possessing heteroatoms.

27. The rock assay of claim 17, further comprising a separation step for separating any catalytically-generated methane from any other hydrocarbon species potentially present after the reaction step.

28. The rock assay of claim 27, wherein the separating is done by condensing the other hydrocarbon species on a cold trap.

29. The rock assay of claim 27, wherein the separating is done via chromatographic means.

30. The rock assay of claim 17, wherein the analysis step involves detecting the presence of catalytically-generated methane using a detection device selected from the group consisting of a flame ionization detector, a mass-selective detector, a spectroscopic detector, an electron capture detector, a thermal conductivity detector, a residual gas analyzer, and combinations thereof.

31. The rock assay of claim 17, wherein ascribing an intrinsic catalytic activity to said sedimentary rock in the analysis step further comprises determining a rate constant, k, associated with a given set of reaction conditions and a reaction duration, as utilized in the reaction step.

32. A rock assay comprising:
a) a sample preparation step for exposing fresh surface of a sedimentary rock sample potentially comprising zero-valent transition metal, wherein the sample preparation step is carried out under inert conditions;

b) a reaction step for exposing the sedimentary rock sample to hydrogen gas and a hydrocarbon material in an exposure environment under assay exposure conditions, wherein such exposure leads to the catalytic generation of methane gas if zero-valent transition metal is present within the sedimentary rock sample, and wherein the sedimentary rock sample, after undergoing the sample preparation step, is not exposed to $O_2$ until after the reaction step;

c) an analysis step for ascertaining the presence of methane catalytically-generated by zero-valent transition metal potentially present in said sedimentary rock sample and, if present, for ascribing an intrinsic catalytic activity to said sedimentary rock corresponding to the assay exposure conditions; and d) a projection step, wherein the intrinsic catalytic activity of the sedimentary rock under assay exposure conditions is projected onto a source reservoir, from which the rock sample originated and having known reservoir conditions, in order to ascertain catalytic oil-to-gas conversion within said reservoir, over geologic timescales, for the purpose of making predictive determinations related to oil and gas exploration.

33. The rock assay of claim 32, wherein the intrinsic catalytic activity is further projected onto a genetically similar reservoir.

34. The rock assay of claim 33, wherein the genetically similar reservoir is distal to the source reservoir.

35. The rock assay of claim 32, wherein an intrinsic catalytic activity of source rock is determined for at least two various depositional environments throughout a stratigraphic source rock unit to provide an oil-gas habitat map of said stratigraphic source rock unit.

36. The rock assay of claim 35, wherein the oil-gas habitat map of said stratigraphic source rock unit is used to predict the distribution of oil and gas in reservoirs in a stratigraphic rock unit proximal to the stratigraphic source rock unit within which oil and gas is generated and expelled into reservoirs within the proximal rock unit.

37. The rock assay of claim 32, wherein the intrinsic catalytic activity of the sedimentary rock sample, from a source reservoir, enables the prediction of oil-gas conversion within conduit rock along an oil migration pathway.

38. The rock assay of claim 32, wherein the sample preparation step involves a grinding process for exposing fresh surface of a quantity of rock sample potentially comprising zero-valent transition metal.

39. The rock assay of claim 32, wherein the exposure environment of the reaction step is static.

40. The rock assay of claim 32, wherein the exposure environment of the reaction step comprises a flow system.

41. The rock assay of claim 32, wherein the assay exposure conditions comprise a temperature of between about 200° C. and about 350° C.

42. The rock assay of claim 32, wherein the assay exposure conditions comprise a hydrogen partial pressure of between about 0.1 torr and about 500 torr.

43. The rock assay of claim 32, wherein the reaction step comprises a duration of between about 1 minute and about 30 days.

44. The rock assay of claim 32, wherein the hydrocarbon material used in the reaction step comprises hydrocarbon species having 2–25 carbon atoms.

45. The rock assay of claim 32, further comprising a separation step for separating any catalytically-generated methane from any other hydrocarbon species potentially present after the reaction step.

46. The rock assay of claim 32, wherein the analysis step involves detecting the presence of catalytically-generated methane using a detection device selected from the group consisting of a flame ionization detector, a mass-selective detector, a spectroscopic detector, an electron capture detector, a thermal conductivity detector, a residual gas analyzer, and combinations thereof.

47. The rock assay of claim 32, wherein ascribing an intrinsic catalytic activity to said sedimentary rock in the analysis step further comprises determining a rate constant, k, associated with a given set of reaction conditions and a reaction duration, as utilized in the reaction step.

48. The rock assay of claim 47, wherein the projection step comprises the determination of rate constants, k, for reaction steps at at least two reaction temperatures, so as to permit generation of a ln k versus T plot which, when calibrated to subsurface conditions, can be extrapolated to yield a rate constant for oil-to-gas conversion in the reservoir, and which is useful for predicting the current content of said reservoir.

49. A method comprising the steps of:
a) providing a sedimentary rock sample potentially comprising a quantity of at least one zero-valent transition metal;
b) processing the sedimentary rock sample to provide freshly exposed surface, wherein the processing is carried out under inert conditions;
c) exposing the sedimentary rock sample to hydrogen gas and a quantity of hydrocarbon material in an exposure environment, the hydrocarbon material comprising hydrocarbon species having at least two carbons, such that methane is catalytically generated if zero-valent transition metal is present within the sedimentary rock sample, and wherein the sedimentary rock sample, once processed, is not exposed to $O_2$ until after such exposing; and
d) detecting any catalytically-generated methane, generated as a result of said exposing, in order to ascertain the presence of zero-valent transition metal within said sedimentary rock sample.

50. The method of claim 49, wherein the processing step involves a grinding process.

51. The method of claim 49, wherein the inert conditions comprise an atmosphere of inert gas, the gas having been scrubbed of oxygen.

52. The method of claim 49, wherein the step of exposing comprises a duration of between about 1 minute and about 30 days.

53. The method of claim 49, wherein the exposure environment is static.

54. The method of claim 49, wherein the exposure environment comprises a flow system.

55. The method of claim 49, wherein the exposure environment comprises a temperature of between about 200° C. and about 350° C.

56. The method of claim 49, wherein the exposure environment comprises a hydrogen partial pressure of between about 0.1 torr and about 500 torr.

57. The method of claim 49, wherein the mass ratio of hydrocarbon material to hydrogen used in the step of exposing is between about 1:1000 and about 1000:1 prior to any potential catalytic decomposition of the hydrocarbon material.

58. The method of claim 49, wherein the hydrocarbon material introduced in the exposing step comprises hydrocarbon species having 2–25 carbon atoms.

59. The method of claim 49, wherein the hydrocarbon material introduced in the exposing step comprises hydrocarbon species possessing heteroatoms.

60. The method of claim 49, further comprising a step of separating any catalytically-generated methane from any other hydrocarbon species potentially present after the step of exposing.

61. The method of claim 60, wherein the separating is done by condensing the other hydrocarbon species on a cold trap.

62. The method of claim 60, wherein the separating is done via chromatographic means.

63. The method of claim 49, wherein detecting the presence of catalytically-generated methane in the step of detecting involves a detection device selected from the group consisting of a flame ionization detector, a mass-selective detector, a spectroscopic detector, an electron capture detector, a thermal conductivity detector, a residual gas analyzer, and combinations thereof.

64. A rock assay comprising the steps of:
 a) providing a sedimentary rock sample potentially comprising a quantity of at least one zero-valent transition metal;
 b) processing the sedimentary rock sample to provide freshly exposed surface, wherein the processing is carried out under inert conditions;
 c) exposing the sedimentary rock sample to hydrogen gas and a quantity of hydrocarbon material in an exposure environment under a set of assay exposure conditions, the hydrocarbon material comprising hydrocarbon species having at least two carbons, such that methane is catalytically generated if zero-valent transition metal is present within the sedimentary rock sample, wherein the sedimentary rock sample, once processed, is not exposed to $O_2$ until after such exposing; and
 d) analyzing the exposure environment for any catalytically-generated methane, generated as a result of said exposing, in order to ascertain the presence of zero-valent transition metal within said sedimentary rock sample and, if present, ascribing an intrinsic catalytic activity to the sedimentary rock for the set of assay exposure conditions.

65. The rock assay of claim 64, wherein the processing step involves a grinding process for exposing fresh surface of a quantity of rock sample potentially comprising zero-valent transition metal.

66. The rock assay of claim 64, wherein the hydrogen gas is scrubbed of oxygen.

67. The rock assay of claim 64, wherein the exposure environment is static.

68. The rock assay of claim 64, wherein the exposure environment comprises a flow system.

69. The rock assay of claim 64, wherein the assay exposure conditions comprise a temperature of between about 200° C. and about 350° C.

70. The rock assay of claim 64, wherein the assay exposure conditions comprise a hydrogen partial pressure of between about 0.1 torr and about 500 torr.

71. The rock assay of claim 64, wherein the step of exposing comprises a duration of between about 1 minute and 30 days.

72. The rock assay of claim 64, wherein the mass ratio of hydrocarbon material to hydrogen introduced in the step of exposing is between about 1:1000 and about 1000:1, prior to any potential catalytic decomposition of the hydrocarbon material.

73. The rock assay of claim 64, wherein the hydrocarbon material used in the exposing step comprises hydrocarbon species having 2–25 carbon atoms.

74. The rock assay of claim 64, wherein the hydrocarbon material used in the exposing step comprises hydrocarbon species possessing heteroatoms.

75. The rock assay of claim 64, further comprising a step of separating any catalytically-generated methane from any other hydrocarbon species potentially present after the exposing step.

76. The rock assay of claim 75, wherein the separating is done by condensing the other hydrocarbon species on a cold trap.

77. The rock assay of claim 75, wherein the separating is done via chromatographic means.

78. The rock assay of claim 64, wherein the step of analyzing involves detecting the presence of catalytically-generated methane using a detection device selected from the group consisting of a flame ionization detector, a mass-selective detector, a spectroscopic detector, an electron capture detector, a thermal conductivity detector, a residual gas analyzer, and combinations thereof.

79. The rock assay of claim 64, wherein ascribing an intrinsic catalytic activity to said sedimentary rock in the step of analyzing further comprises determining a rate constant, k, associated with a given set of reaction conditions and a reaction duration, as utilized in the reaction step.

80. A rock assay comprising the steps of:
 a) providing a sedimentary rock sample potentially comprising a quantity of at least one zero-valent transition metal;
 b) processing the sedimentary rock sample to provide freshly exposed surface, wherein the processing is carried out under inert conditions;
 c) exposing the sedimentary rock sample to hydrogen gas and a quantity of hydrocarbon material in an exposure environment under a set of assay exposure conditions such that methane is catalytically generated if zero-valent transition metal is present within the sedimentary rock sample, wherein the sedimentary rock sample, once processed, is not exposed to $O_2$ until after such exposing; and
 d) analyzing the exposure environment for any catalytically-generated methane, generated as a result of said exposing, in order to ascertain the presence of zero-valent transition metal within the sedimentary rock sample and, if present, ascribing an intrinsic catalytic activity to the sedimentary rock corresponding to the set of assay exposure conditions; and
 e) projecting onto a source reservoir from which the sedimentary rock sample was removed, and for which reservoir conditions are known, the calibrated catalytic activity determined for the sedimentary rock sample under the set of assay exposure conditions in order to ascertain the extent of oil-to-gas conversion within the reservoir over geological timescales for the purpose of making predictive determinations related to oil and gas exploration.

81. The rock assay of claim 80, wherein the intrinsic catalytic activity is further projected onto a genetically similar reservoir.

82. The rock assay of claim 81, wherein the genetically similar reservoir is distal to the source reservoir.

83. The rock assay of claim 80, wherein an intrinsic catalytic activity of source rock is determined for at least two various depositional environments throughout a stratigraphic source rock unit to provide an oil-gas habitat map of said stratigraphic source rock unit.

84. The rock assay of claim 83, wherein the oil-gas habitat map of said stratigraphic source rock unit is used to predict the distribution of oil and gas in reservoirs in a stratigraphic rock unit proximal to the stratigraphic source rock unit within which oil and gas is generated and expelled into reservoirs within the proximal rock unit.

85. The rock assay of claim 80, wherein the intrinsic catalytic activity of the sedimentary rock sample, from a source reservoir, enables the prediction of oil-gas conversion within conduit rock along an oil migration pathway.

86. The rock assay of claim 80, wherein the processing step involves a grinding process for exposing fresh surface of a quantity of rock sample potentially comprising zero-valent transition metal.

87. The rock assay of claim 80, wherein the exposure environment is static.

88. The rock assay of claim 80, wherein the exposure environment comprises a flow system.

89. The rock assay of claim 80, wherein the assay exposure conditions comprise a temperature of between about 200° C. and about 350° C.

90. The rock assay of claim 80, wherein the assay exposure conditions comprise a hydrogen partial pressure of between about 0.1 torr and about 500 torr.

91. The rock assay of claim 80, wherein the step of exposing comprises a duration of between about 1 minute and 30 days.

92. The rock assay of claim 80, wherein the hydrocarbon material used in the exposing step comprises hydrocarbon species having 2–25 carbon atoms.

93. The rock assay of claim 80, wherein the hydrocarbon material used in the exposing step comprises a gaseous hydrocarbon species.

94. The rock assay of claim 80, further comprising a step of separating any catalytically-generated methane from any other hydrocarbon species potentially present after the step of exposing.

95. The rock assay of claim 80, wherein the step of analyzing involves detecting the presence of catalytically-generated methane using a detection device selected from the group consisting of a flame ionization detector, a mass-selective detector, a spectroscopic detector, an electron capture detector, a thermal conductivity detector, a residual gas analyzer, and combinations thereof.

96. The rock assay of claim 80, wherein ascribing an intrinsic catalytic activity to said sedimentary rock in the analysis step further comprises determining a rate constant, k, associated with a given set of reaction conditions and a reaction duration, as utilized in the reaction step.

97. The rock assay of claim 96, wherein the step of projecting further comprises the determination of rate constants, k, for reaction steps at at least two reaction temperatures, so as to permit generation of a ln k versus T plot which can be extrapolated to yield a rate constant for oil-to-gas conversion in the reservoir, and which is useful for predicting the current content of said reservoir.

* * * * *